United States Patent [19]
Ortiz et al.

[11] Patent Number: 5,163,945
[45] Date of Patent: Nov. 17, 1992

[54] SURGICAL CLIP APPLIER

[75] Inventors: Mark S. Ortiz, Milford, Ohio; Michael S. Cropper, Edgewood, Ky.; William J. Zwaskis, Fanwood, N.J.; Richard F. Schwemberger, Cincinnati, Ohio

[73] Assignee: Ethicon, Inc.

[21] Appl. No.: 780,744

[22] Filed: Oct. 18, 1991

[51] Int. Cl.⁵ ............................................. A61B 17/00
[52] U.S. Cl. ................................. 606/142; 606/139; 227/901
[58] Field of Search ................ 606/139, 142; 227/901

[56] References Cited

U.S. PATENT DOCUMENTS

| | | | |
|---|---|---|---|
| 3,270,745 | 9/1966 | Wood | 606/142 |
| 3,631,707 | 1/1972 | Miller | 606/142 |
| 3,926,195 | 12/1975 | Bleier et al. | 606/157 |
| 4,226,242 | 11/1980 | Jarvik | 606/143 |
| 4,296,751 | 10/1981 | Blake, III et al. | 606/143 |
| 4,361,229 | 11/1982 | Mericle | 206/339 |
| 4,418,694 | 12/1983 | Beroff et al. | 606/158 |
| 4,434,795 | 3/1984 | Mericle | 606/142 |
| 4,476,865 | 10/1984 | Failla et al. | 606/158 |
| 5,030,226 | 1/1989 | Green et al. | 606/158 |
| 5,100,416 | 3/1992 | Ott et al. | 606/139 |

Primary Examiner—Stephen C. Pellegrino
Assistant Examiner—Gary Jackson
Attorney, Agent, or Firm—Dressler, Goldsmith, Shore, Sutker & Milnamow, Ltd.

[57] ABSTRACT

A surgical device and cooperating cartridge for applying surgical clips during endoscopic surgery. The surgical device incluces a jaw assembly, a barrel assembly, and a handle assembly. The jaw assembly has movable jaw members, each including a substantially transverse grooved portion and at least one angular side shield extending inwardly from an upper and a lower portion of the jaw member. The jaw members are oriented at an angle of approximately 22° relative to the longitudinal axis of the barrel portion. The distal surface of each jaw member is oriented at an angle that extends distally and outwardly. The jaw members are insertable into a unique cooperating cartridge that retains the surgical clip.

12 Claims, 8 Drawing Sheets

SURGICAL CLIP APPLIER

FIELD OF THE INVENTION

This invention relates generally to a surgical clip applier and a cooperating surgical clip cartridge; and more particularly, the invention relates to an applier device and cartridge for receiving and applying a clip adapted to replace a suture knot during laparoscopic or endoscopic surgery.

BACKGROUND OF THE INVENTION

As medical and hospital costs continue to increase, surgeons are constantly striving to develop advanced surgical techniques. Advances in the surgical field are often related to the development of operative techniques that involve less invasive surgical procedures and reduce overall patient trauma. In this manner, the length of hospital stays can be significantly reduced, and therefore the hospital and medical costs can be reduced as well.

One of the truly great advances in recent years to reduce the invasiveness of surgical procedures is endoscopic surgery. Endoscopic surgery involves the use of an endoscope, which is an instrument permitting the visual inspection and magnification of a body cavity. The endoscope is inserted through a cannula after puncture through the wall of the body cavity with a trocar assembly that includes a sharp-pointed obturator. The surgeon can then perform diagnostic and therapeutic procedures at the surgical site with the aid of specialized instrumentation designed to fit through additional trocars providing small diameter openings into the desired body cavity as may be required.

An age-old procedure that surgeons are required to perform to repair or reconstruct traumatized body tissue is suturing. Fortunately, medical instruments have been recently designed to allow a surgeon to manipulate a suture, or suture and needle combination, through the small diameter opening of a cannula. However, the ability to tie an appropriately placed suture knot has become troublesome and problematical.

It is known to use hemostatic clips and clip appliers to ligate blood vessels and other tubular members. Such hemostatic clips and clip appliers are described, for example, in U.S. Pat. Nos. 4,418,694, 4,476,865 and 5,030,226.

In View of the deficiencies of the prior art for creating a useful alternative to tying a suture knot, what is desired within the medical community is a device suitable for application using endoscopic techniques that can successfully replace the suture knot. More specifically, what is needed is a surgical clip and clip applier system particularly adapted for replacing a suture knot during endoscopic surgery and which exhibits adequate clamping force to function effectively.

A surgical clip particularly adapted for use with the present invention is disclosed in commonly assigned U.S. patent application Ser. No. 717,297, filed on Jun. 18, 1991, by C. Chen et al. In order to more readily apply a surgical clip using endoscopic techniques, it is desired to provide an improved cartridge for holding such surgical clips, and an improved surgical clip applier that is insertable into the cartridge for grasping and removing such surgical clips and is then insertable through a trocar tube for applying such surgical clips during endoscopic surgery. In particular, what is needed is an improvement in surgical clip cartridges and appliers that are designed to handle and apply the recently-developed surgical clip having opposed, hinged leg portions which are movable between an open position and a closed position.

SUMMARY OF THE INVENTION

In accordance with the principles of the present invention, a surgical device is provided for applying a surgical clip having opposed, hinged leg portions that are movable between an open position and a closed position. The leg portions of the surgical clip have boss portions that extend outwardly therefrom. The surgical clip applier includes a pair of spaced apart, opposing jaw members having clip receiving/closing portions that are movable between an open position, for receiving the leg portions of a surgical clip in their open position, and a closed position, wherein the leg portions of the surgical clip are in their closed position. The jaw members have side shield means extending inwardly toward the opposing jaw for contacting an upper and a lower surface of the surgical clip so as to retain the surgical clip therebetween.

The clip receiving/closing portions of the jaw members define substantially transverse grooved portions for receiving and gripping the boss portion of the surgical clip. A partially cylindrical grooved portion is defined by a proximal edge and a distal edge. The proximal edge is located inwardly of the distal edge. The clip receiving/closing portions of the jaw members are oriented at an angle of approximately 22 degrees relative to the longitudinal axis of the device for convenience in locating and positioning the surgical clip during surgery.

The distal surface of each jaw member is oriented so as to extend distally and outwardly to cause the closing of the hinged leg members of the surgical clip as the distal surfaces are pressed against the boss members of the surgical clip during loading of a clip into the applier.

The jaw members have arm portions that extend proximally from the clip receiving/closing portions. Each arm portion has a cam surface oriented at an angle that extends proximally and inwardly. A former means envelops a part of the arm portions for sliding over the cam surfaces so as to move the jaw members between their open and closed positions.

A barrel member envelops a proximal portion of the former means. The arm portions of the jaw members extend proximally into the barrel member. The proximal ends of the arm portions are affixed to the barrel member to prevent axial and/or rotational movement of the jaw members relative to the barrel member. The barrel member is rotatable to permit rotation of both the barrel member and the jaw members.

The surgical device cooperates with a unique cartridge that stores the clips. The cartridge includes cavities formed therein to receive and retain the clips. The cavities are configured to retain the clips and permit the insertion of the jaw members thereinto to remove the clips therefrom.

BRIEF DESCRIPTION OF THE DRAWINGS

A more complete appreciation of this invention, and many of the attendant advantages thereof, will be readily apparent as the same becomes better understood by reference to the following detailed description when considered in conjunction with the accompanying drawings in which like reference numerals indicate the same or similar components, wherein.

DETAILED DESCRIPTION OF THE PREFERRED EMBODIMENT

Figure 1:
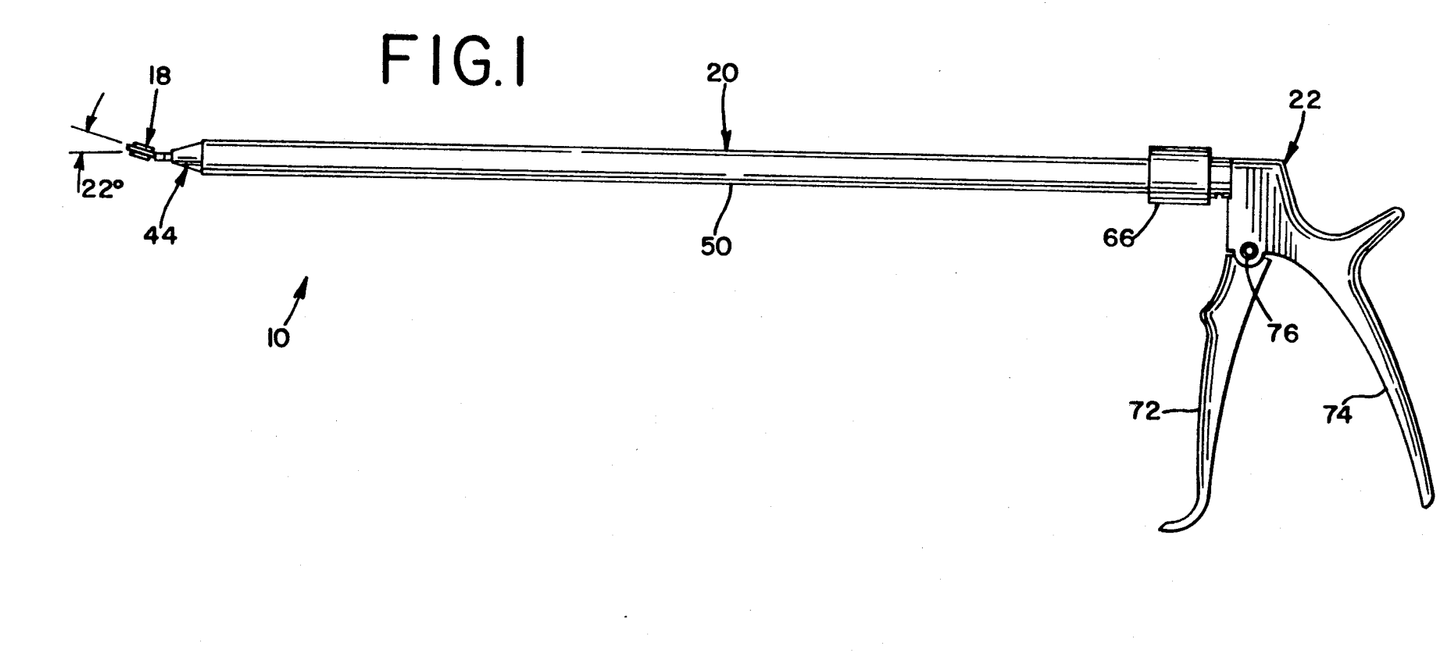
FIG. 1 is a side elevational view of a surgical clip applier constructed in accordance with the present invention.
Figure 2:
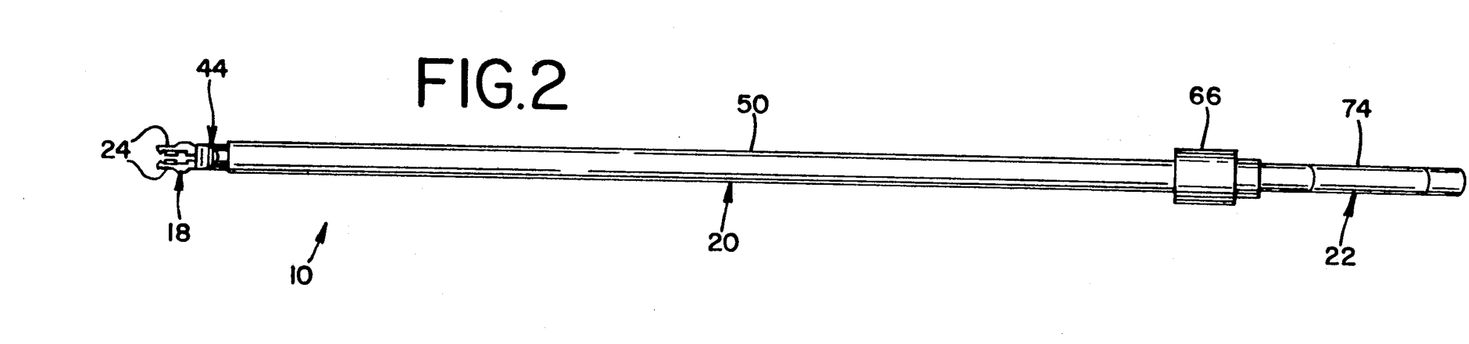
FIG. 2 is a top view of the surgical clip applier shown in FIG. 1.
Figures 3, 4, 5, 6:
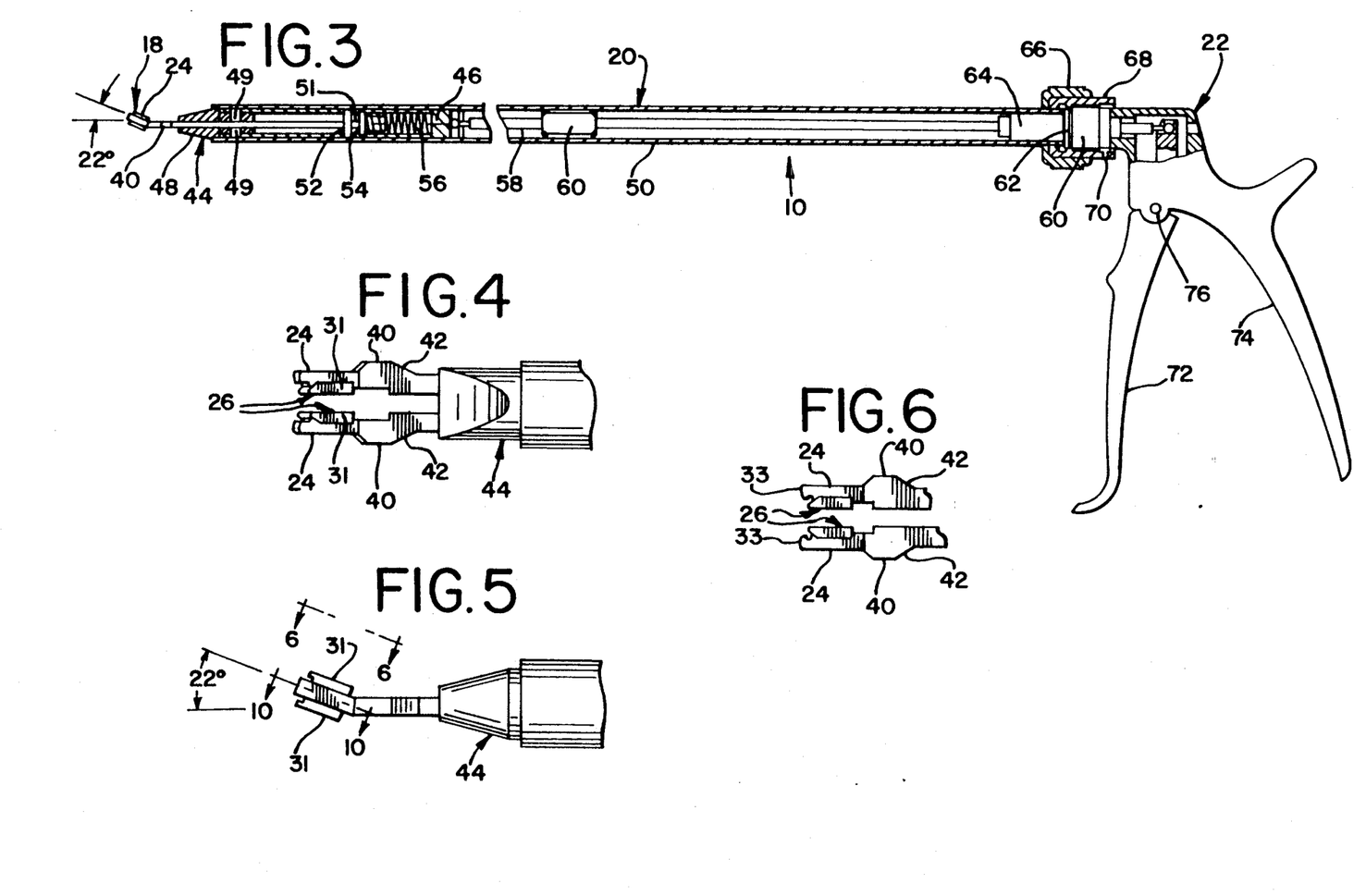
FIG. 3 is a side elevational view of the surgical clip applier as shown in FIG. 1, with portions of the barrel portion and handle portion shown in cross-section to illustrate interior detail.
FIG. 4 is an enlarged fragmentary top view of the jaw portion of the surgical clip applier.
FIG. 5 is a side elevational view of the jaw portion of the surgical clip applier shown in FIG. 4.
FIG. 6 is a fragmentary view of the jaw portion taken along the plane 6—6 in FIG. 5.
Figure 8:
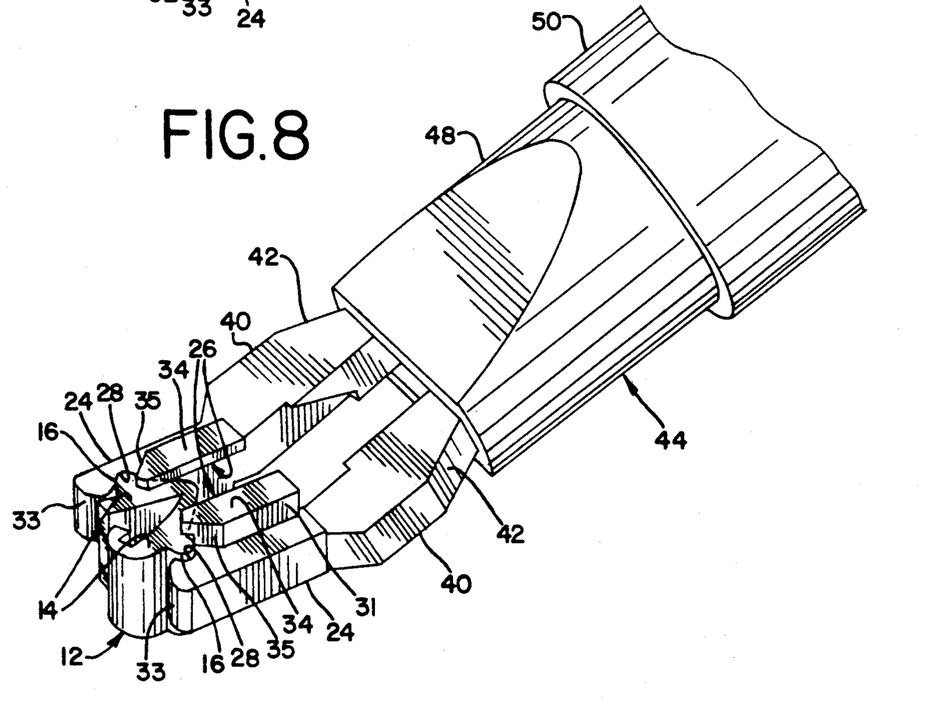
FIG. 8 is a perspective view as shown in FIG. 7 with a surgical clip inserted in the clip receiving/closing portions of the jaw members.
Figure 10:
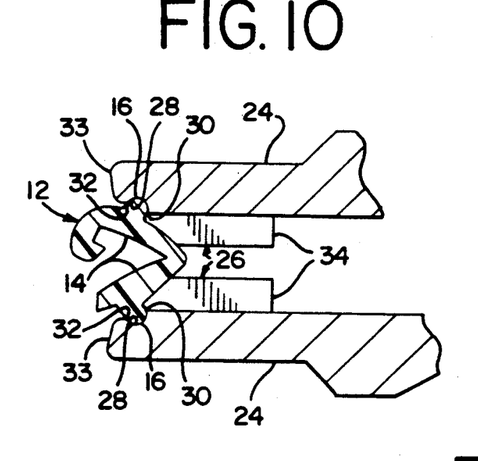
FIG. 10 is a cross-sectional view of the jaw members taken along the plane 10—10 in FIG. 5 with a surgical clip inserted in the clip receiving/closing portions thereof.
Figure 11:
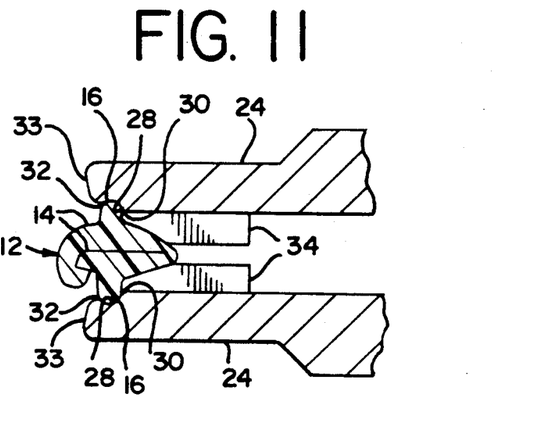
FIG. 11 is a cross-sectional view similar to FIG. 10 with the clip receiving/closing portions in the closed position.

Referring to FIGS. 1-3, there is shown a surgical device 10 for applying a surgical clip, and which is particularly adapted for use in applying a clip to a suture during an endoscopic procedure, instead of forming a knot in the suture. As shown in FIGS. 8, 10 and 11, a surgical clip 12, of the type utilized by device 10, has opposed, hinged leg portions 14 that are movable between an open position, as shown in FIGS. 8 and 10, and a closed position, as shown in FIG. 11. The leg portions of the surgical clip have a boss portion 16 extending outwardly therefrom. A detailed description of the surgical clip is found in above mentioned U.S. patent application Ser. No. 717,297, which description is incorporated herein by reference. The surgical device of this invention is particularly usable as an applier of such a surgical clip.

The surgical device 10 generally consists of a jaw assembly 18, a barrel assembly 20, and a handle assembly 22, as best seen in FIGS. 1, 2 and 3.

Referring to FIGS. 2, 4, 6-11 and 13, the jaw assembly 18 includes a pair of spaced apart, opposing jaw members 24. The jaw members have clip receiving/closing portions 26 that are movable between an open position for receiving the leg portions 14 of the surgical clip 12 in their open position, as seen in FIGS. 4, 6-8, and 10, and a closed position wherein the leg portions of the surgical clip are in their closed position, as seen in FIG. 11. The clip receiving/closing portions are preferably oriented at an angle relative to the longitudinal axis of the barrel portion. An angle is preferred by surgeons for facilitating the proper positioning of the surgical clip during surgery. Preferably the angle is approximately 22 degrees.

The clip receiving/closing portions 26 have a substantially transverse grooved portion 28 for receiving and gripping a boss portion 16 of the surgical clip 12, as shown in FIGS. 7, 8, 10 and 11. Preferably, the grooved portion has the same general shape as the corresponding boss portion. In the best mode known to the inventors, both the grooved portion and the boss portion are partially cylindrical. Grooved portion 28 defines a proximal edge 30 and a distal edge 32. Preferably, the proximal edge 30 is located inwardly of the distal edge 32 to form a backstop against proximal movement of the surgical clip 12.

Figure 16:
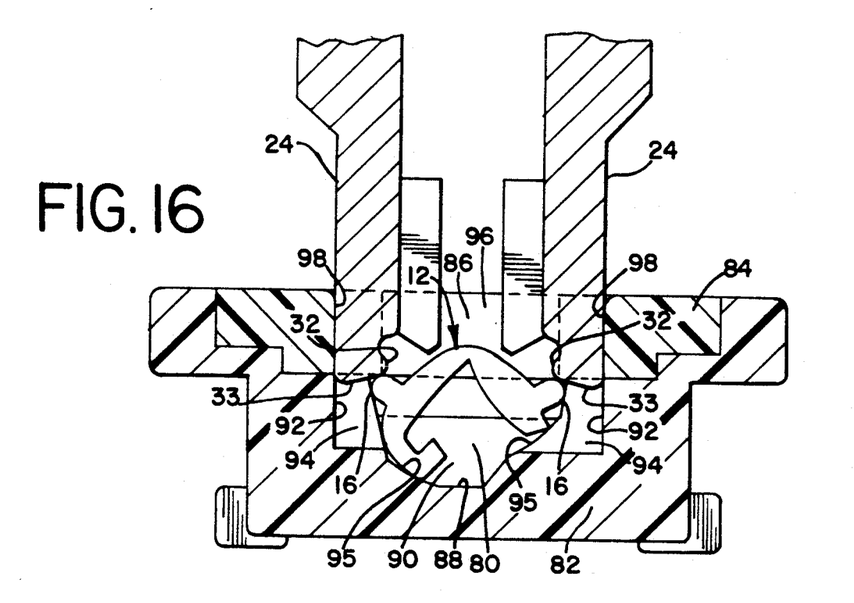
FIGS. 16 through 18 are a series of enlarged cross-sectional views taken along the plane 15—15 in FIG. 12 of a cavity of the cartridge with the jaw members and surgical clip inserted therein to show a sequence of the movement of the jaw members and surgical clip as the jaw members descend into the cavity and grip the surgical clip.
Figure 17:
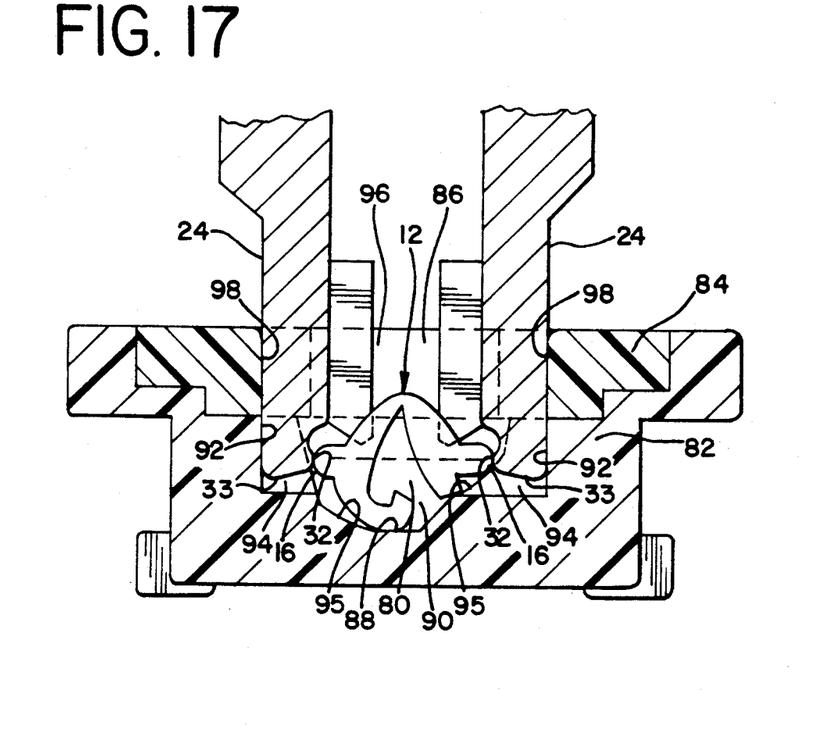

The distal surface 33 of each jaw member 24 is preferably oriented at an angle that extends distally and outwardly. Thus, when a clip is being loaded into the applier, the distal surfaces are pressed against the boss portions 16 of the surgical clip 12, and the hinged leg portions 14 of the surgical clip 12 are caused to partially close to permit the insertion of the surgical clip between the jaw members and the insertion of the boss portions into the grooved portions, as shown in FIGS. 16 and 17 and further described hereinbelow.

Figure 7:
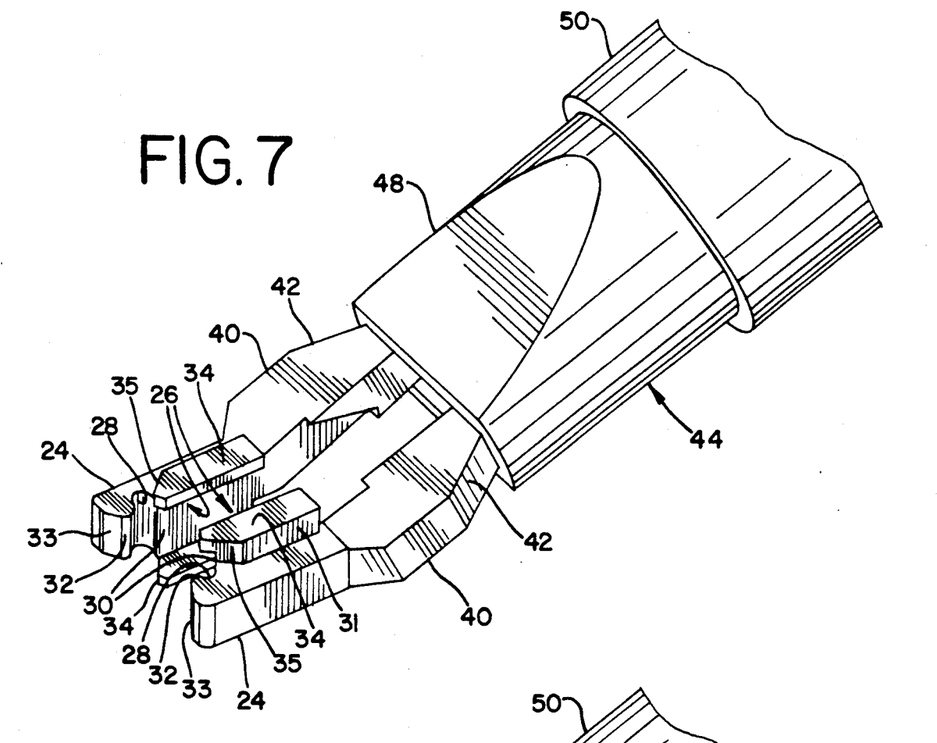
FIG. 7 is a further enlarged perspective view of the jaw portion and a part of the barrel assembly of the surgical clip applier.

The jaw members 24 have side shield means 31 extending inwardly toward the opposing jaw member for contacting an upper and a lower surface of the surgical clip 12 so as to retain the surgical clip therebetween. Preferably, the side shield means includes a plurality of angular flanges 34 that extend inwardly from the upper and lower surfaces of the jaw members toward an opposing jaw member, as shown in FIGS. 7, 8, 10 and 11. In the best mode known to the inventors, a pair of offset elevated flanges extend respectively above and below the upper and lower surfaces of each jaw member. Thus configured, the jaw members and flanges generally define a key-shape in transverse cross-section. The distal ends of the flanges define a surface 35 that extends distally and inwardly, as shown in FIGS. 7 and 8. However, other flange arrangements, including only one flange contacting the upper surface of the surgical clip and only one flange contacting the lower surface of the surgical clip, may also be utilized.

The side shield means 31 also functions to protect the surgical clip from contact with tissue and debris while the surgeon is moving and positioning the surgical clip during surgery. The flanges 34 extend inwardly and partially cover the upper and lower surfaces of the surgical clip 12, and may be of varying lengths and widths to suitably cover and protect the upper and lower surfaces of the surgical clip. The side shield means are also useful for pressing against adjacent tissue to temporarily displace the tissue in order to facilitate better access to the desired location and position for applying the surgical clip. In the illustrated embodiment, the clip engaging surfaces of the flanges are flat, parallel and spaced by a dimension slightly greater than the thickness of the clip to facilitate initial loading of the clip into the applier and subsequent application of the clip to a suture.

Figure 9:
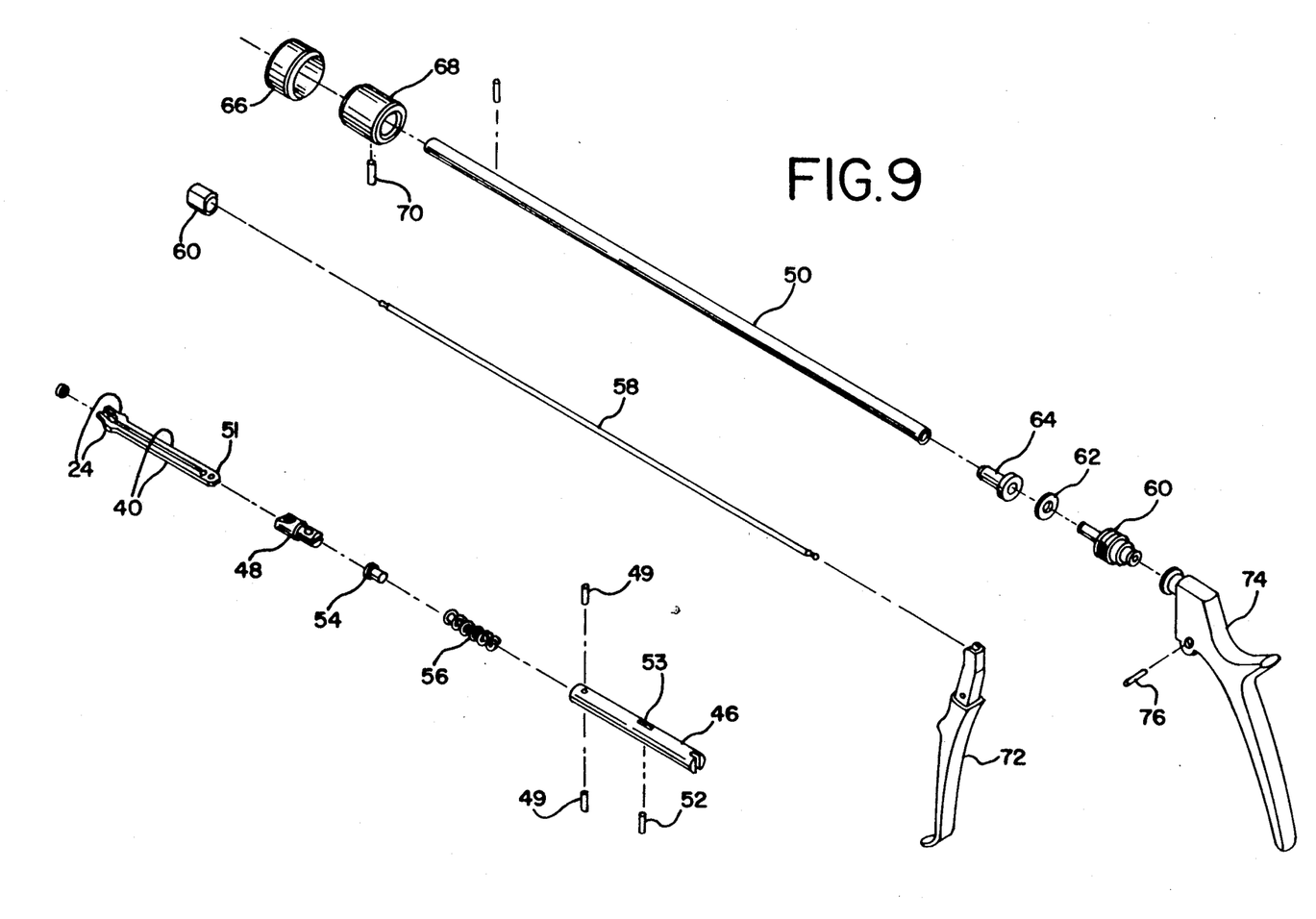
FIG. 9 is an exploded, schematic view of the surgical clip applier.

Referring to FIGS. 3-9, arm portions 40 of the jaw members 24 extend proximally from the clip receiving/closing portions 26. The arm portions are connected to each other at their proximal end portions 51, as seen in FIG. 9. The arm portions are flexible so as to permit movement of the jaw members between their open and closed positions. The arm portions are constructed so as to bias the jaw members toward their open position. Each arm portion 40 is formed with a cam surface 42 oriented at an angle that extends proximally and inwardly. Preferably, the cam surface is located adjacent to and distally of the clip receiving/closing portions 26.

Figure 14:
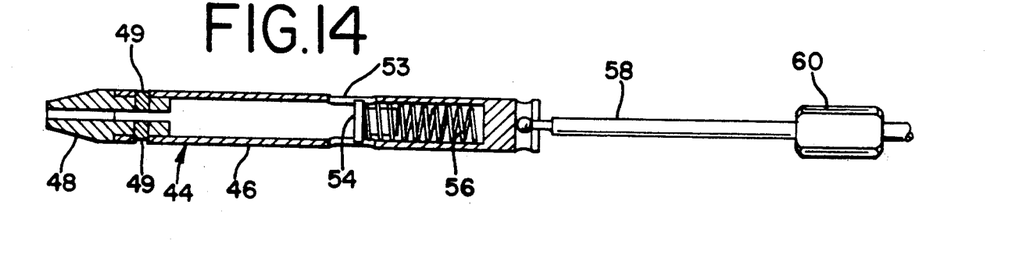
FIG. 14 is a side view of the former assembly, spring plate, spring and drive rod of the surgical clip applier, with the former assembly shown in cross-section to illustrate interior detail.

Referring to FIGS. 3 and 14, former assembly 44 envelopes a part of the arm portions 40 and includes a former member 46 having an insert 48 extending distally therefrom. Former member 46 is connected to the insert 48 with a pair of former pins 49. Former member 46 is tubular so as to permit insertion of the proximal end of insert 48 thereinto.

Former assembly 44 slides axially in a forward and rearward direction over the cam surfaces 42 of the arm portions 40. When the former assembly is in the rear position, the jaw members 24 are in their open position, as shown in FIGS. 4, 7, 8, 10 and 13. As the former assembly slides forwardly, the distal end portion of insert 48 contacts the cam surfaces and causes the jaw members to close, as shown in FIG. 11. Thus, the former assembly slides forwardly and rearwardly over the cam surfaces to control the movement of the jaw members between their open and closed positions.

Barrel assembly 20 includes a barrel member 50 that envelops a proximal portion of the former assembly 44 and extends proximally therefrom. The insert 48 extends distally from the distal end of barrel member 50. A rotation knob 66 is affixed to the proximal end of the barrel member. Arm portions 40 of the jaw members 24 extend proximally into the barrel member. The proximal end portions 51 of the arm portions are affixed to barrel member 50 by a ferrule pin 52 so as to prevent axial and rotational movement of the jaw members 24 relative to the barrel member. The ferrule pin extends transversely through slots 53 in the former member 46 so as to permit axial movement of the former member, as best seen in FIGS. 9 and 14.

A spring plate 54 and spring 56 are located within the former member 46. The spring plate abuts the proximal end portions 51 of the arm portions. Spring 56 extends proximally from the spring plate and contacts the interior face of the rear surface of the former member 46. Spring 56 is compressed for biasing the former assembly 44 toward its rear position.

A drive rod 58 is connected to the proximal end of former member 46 by a ball joint connection. Drive rod 58 extends proximally from the former member within the interior of the barrel member 50. A bushing 60 operates to center the drive rod 58 within the barrel member.

Drive rod 58 is movable between a forward position and a rearward position so as to actuate the former assembly 44 between its forward position and rearward position.

Handle assembly 22 of the surgical device extends proximally from the barrel assembly 20 and rotatably receives the proximal end of the barrel member 50. Barrel member 50 rotates relative to the handle assembly so as to permit rotation of the jaw assembly 18 relative to the handle assembly. The rotatable connection may be any suitable connection that connects the barrel assembly 20 to the handle assembly, and permits rotation of the barrel assembly relative to the handle assembly.

Handle assembly 22 includes a trigger member 72 that is connected to the proximal end of the drive rod 58 by a ball joint connection. Trigger member 72 is pivotally connected to a handle member 74 by a pivot pin 76 so as to permit pivoting of the trigger relative to the handle. Movement of the trigger member towards the handle member moves the drive rod from a rear position to a forward position and actuates the movement of the former assembly 44 between its rear position and its forward position, thus actuating the movement of the jaw members 24 between their open and closed positions.

The surgical clip applier device of this invention may be constructed from a variety of suitable materials known to those skilled in the art. In the best mode of construction known to the inventors, the bushings and ring washers are constructed from a hard plastic having a smooth surface, and all other parts are constructed from stainless steel. For disposable applications, the surgical device may be constructed from a variety of materials which are suitable for disposable surgical devices.

The surgical clip applier device 10 of the present invention may be used by a surgeon during endoscopic surgery wherein an endoscope is inserted through a cannula after puncture through the wall of the body cavity with a trocar assembly. At the end of suturing, the surgeon applies the surgical clips 12 to the sutures in substitution for knotting of the sutures.

Specifically, while the surgical clip is retained in the jaw members of the surgical clip applier, the surgeon inserts the surgical clip applier through a trocar tube and manipulates the handle assembly 22 and rotation knob 66 to position the surgical clip in the appropriate location. In order to close the surgical clip, the surgeon squeezes the trigger 72 which actuates the former assembly 44 and closes the jaw members 24 as discussed above. After the surgical clip is closed, the surgeon releases the trigger to allow the former assembly to return to its rear position, which in turn allows the jaw members to return to their open position. When the jaw members open, the surgical clip remains closed and locked, as further discussed in U.S. patent application Ser. No. 717,297. Thus, the jaw members release their grip on the surgical clip, and the surgeon may remove the surgical device from the cannula.

Referring to FIGS. 12, 13, and 15-19, the surgical clips are stored in cavities 80 in a cartridge 78. Cartridge 78 in accordance with the invention includes a base member 82 having cavities 80 formed therein and a retainer member 84 having openings 86 formed therein that are in alignment with and configured to correspond to the configuration of the cavities 80. Retainer member 84 is attached to base member 82 in a suitable manner, such as a press fit connection.

Each cavity 80 in the base member 82 is defined by a floor portion 88 having a pair of upstanding, opposed, parallel side walls 90 that are adjacent the side surfaces of the surgical clip and a pair of upstanding, opposed, parallel end walls 92 that are adjacent the boss portions 16 of the surgical clip.

Extending inwardly into each cavity 80 from the intersection of the corners formed at the side and end walls are spacer portions 94 that contact the boss portions of the surgical clip so as to define a generally key-shaped cavity that locates the surgical clip in the cavity in a spaced relationship to the end walls 92. The spaces between the surgical clip and the end walls of the cavity permit the passage of the jaw members 24 therebetween.

Figure 18:
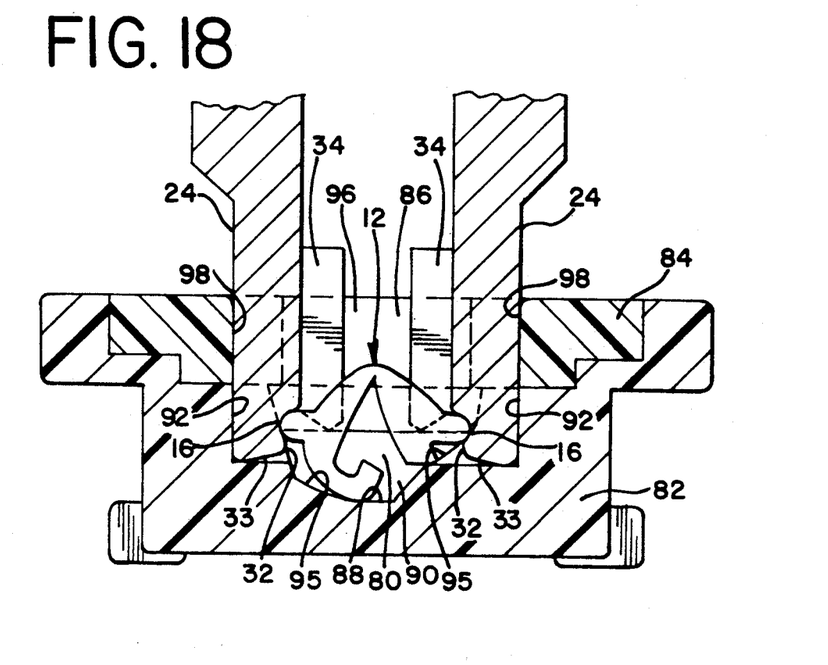
Figure 19:
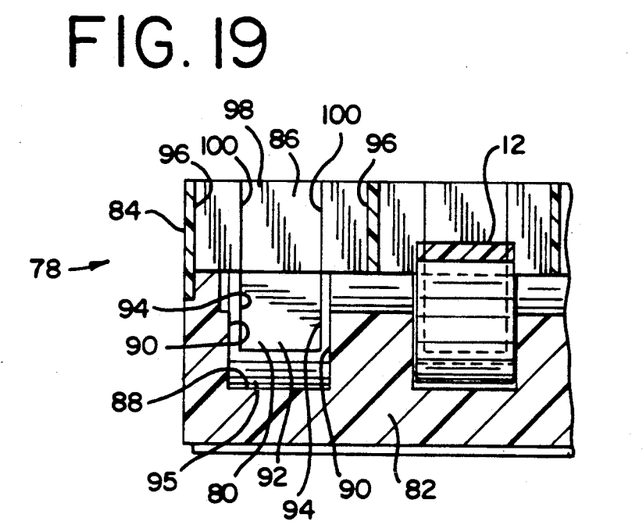
FIG. 19 is an enlarged cross-sectional view taken along the plane 19—19 in FIG. 12 showing a surgical clip in one of the cavities.

Preferably, the side walls 90 of the cavity 80 in the base member 82 extend upwardly from the floor portion 88 only a short distance so as to abut and retain the lower portion of the side surfaces of the surgical clip. Thus configured, the side walls will not interfere with the side shield flanges 34 of the jaw members 24 which extend partially into the cavity, as best shown in FIG. 18.

The floor portion 80 and each spacer portion 94 is formed with a curved ramp portion 95 which conforms to and supports the hinged leg portions 14 of the surgical clip. The curvature of the ramp portion follows the movement of the hinged members as they partially open and close within the cavity, so that the hinge point of the clip remains relatively fixed and the ramp portion remains in substantially constant contact with the hinged members while the hinged members are partially opened and closed within the cartridge.

The openings 86 in the retainer member 84 are defined by parallel side walls 96 and parallel end walls 98. The surgical clip is inwardly spaced from the walls defining the opening 86 to permit the passage of the jaw members 24 and side shield flanges 34 therebetween and to define a generally key-shaped opening that guides the jaw members into the cavity.

Figure 15:
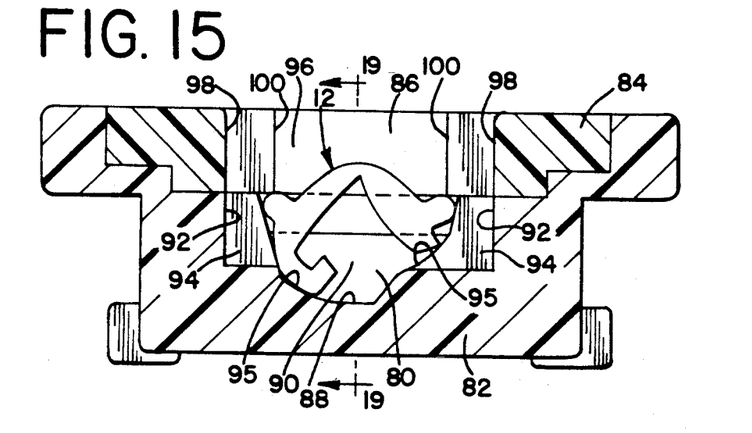
FIG. 15 is an enlarged cross-sectional view taken along the plane 15—15 in FIG. 12 of a cavity of the cartridge with a surgical clip inserted therein.

Extending inwardly from the four corners at the intersection of the side walls 96 and end walls 98 of the openings 86 in the retainer member 84 are retaining lip portions 100 which contact and slightly overlap the boss portions of the surgical clip. The retaining lips function to retain the surgical clip in contact with the base member of the cartridge, as best shown in FIG. 15.

Figures 12, 13:
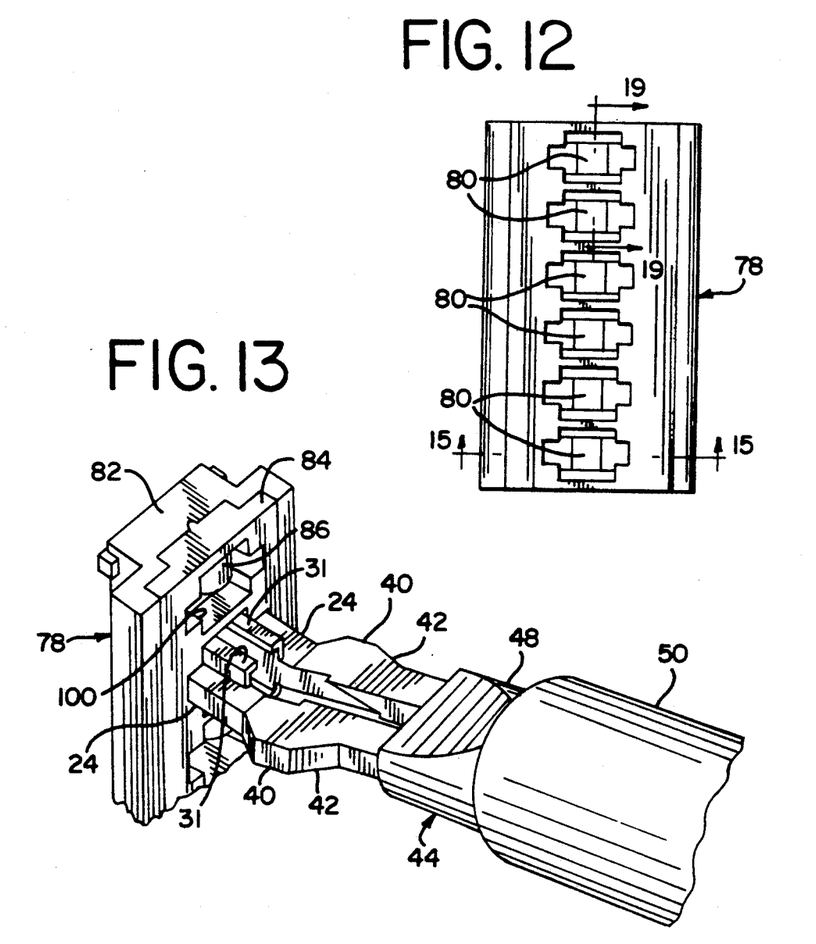
FIG. 12 is a top view of a clip cartridge usable with the applier of the present invention.
FIG. 13 is a perspective view of the cartridge with the jaw portion of the surgical clip applier inserted into a clip receiving cavity in the cartridge.

In order to remove a surgical clip from a cavity 80 in the cartridge 78, the jaw members 24 of the clip applier 10 are inserted into the cavity, as shown in FIG. 13. The walls 90 and 92 of the cavity 80, the spacer portions 94, the walls 96 and 98 of the opening 86 in the retainer member 84, and the retaining lip portions 100 function together to guide the insertion of the jaw members 24 and side shield flanges 34 into the cavity, similar to the insertion of a key into a key hole.

As the jaw members 24 descend into the cavity 80, their distal surfaces 33 press against the boss members 16 of the surgical clip, as shown in FIG. 16. The angled distal surface 33 causes the clip to close slightly as the jaw members press against the boss portions, thus allowing the distal edge 32 of the grooved portion of the jaw member to pass by the boss portion of the clip, as shown in FIG. 17. When the jaw members have fully descended into the cavity, the hinged members of the clip reopen slightly and the grooved portions of the jaw members grip the boss portions 16 of the clip, as shown in FIG. 18. However, the jaw members do not permit the clip to reopen fully and therefore cause the boss portions of the clip to remain inwardly of the retaining lips 100. Thus, the clip is free to be removed from the cavity of the cartridge as the jaw members grip and remove the clip from the cartridge.

The cartridge ma be constructed from any suitable rigid material. In the best mode known the inventors, the cartridge is molded from a suitable plastic material.

From the foregoing, it will be observed that numerous modifications and corrections can be effected without departing from the true spirit and scope of the novel concepts of the present invention. It will be understood that the appended claims are not intended to be limited to the specific embodiment illustrated herein and that the appended claims are intended to cover all such modifications as fall within the scope of the claims.

What is claimed is:

1. A surgical device for applying a surgical clip having opposed, hinged leg portions that are movable between an open position and a closed position; said surgical device comprising:
    a pair of spaced apart, opposing jaw members having clip receiving/closing portions including upper and lower surfaces that are movable between an open position for receiving the leg portions of a surgical clip in their open position therebetween and a closed position wherein the leg portions of the surgical clip are received therebetween in their closed position; said jaw members having side shield means extending inwardly toward an opposing jaw for contacting an upper and a lower surface of a surgical clip so as to retain the surgical clip therebetween; said side shield means including a pair of opposed angular flanges that extend inwardly from the upper and lower surfaces of said jaw members; and said flanges extending upwardly from the upper surfaces of said jaw members and downwardly from the lower surfaces of said jaw members so as to generally define a key-shape in transverse cross-section.

2. A surgical device in accordance with claim 1 wherein said flanges have a distal end that defines a surface that extends distally and inwardly.

3. A surgical device in accordance with claim 1 wherein at least one of said clip receiving/closing portions defines a substantially transverse grooved portion for receiving and gripping the boss portion of a surgical clip.

4. A surgical device in accordance with claim 3 wherein said grooved portion is defined by a proximal edge and a distal edge, said proximal edge being located inwardly of said distal edge.

5. A surgical device in accordance with claim 4 wherein said grooved portion is partially cylindrical.

6. A surgical device in accordance with claim 5 wherein each of said jaw members has an arm portion extending proximally from said clip receiving/closing portion, said arm portion having a cam surface oriented at an angle extending proximally and inwardly, and a former means enveloping a portion of said arm portions for sliding over said cam surfaces so as to cause said jaw members to move between their open and closed portions.

7. A surgical device in accordance with claim 6 including a barrel member enveloping a proximal portion of said former means and extending distally therefrom.

8. A surgical device in accordance with claim 7 wherein said arm portions of said jaw members extend proximally into said barrel member, each of said arm portions having a proximal end that is affixed to said barrel member to prevent axial movement of said jaw members relative to said barrel member.

9. A surgical device in accordance with claim 8 wherein each of said proximal ends of said arm portions are affixed to said barrel member to prevent rotational movement of said jaw members relative to said barrel.

10. A surgical device in accordance with claim 9 wherein said barrel member is rotatable so as to permit rotation of said barrel member and said jaw members.

11. A surgical device in accordance with claim 7 wherein said clip receiving/closing portions of said jaw members are oriented at angle of approximately 22 degrees relative to the axis of said barrel member.

12. A surgical device in accordance with claim 3 wherein each of said jaw members has a distal end surface, said distal end surface being oriented at an angle that extends distally and outwardly to cause the closing of the hinged leg portions of a surgical clip as said distal surfaces are pressed against the boss members of a surgical clip, said distal end surfaces of said jaw members extending distally beyond the distal ends of said flanges.

* * * * *